(12) United States Patent
Choi et al.

(10) Patent No.: US 9,206,449 B2
(45) Date of Patent: Dec. 8, 2015

(54) PROCESS OF BIOLOGICALLY PRODUCING A P-HYDROXYBENZOIC ACID

(71) Applicant: Samsung Electronics Co., Ltd., Suwon-si, Gyeonggi-do (KR)

(72) Inventors: Won Jae Choi, Seongnam-si (KR); Jong Won Byun, Suwon-si (KR); Jin Ho Ahn, Seongnam-si (KR); Young Wan Ha, Seoul (KR); Joo-Hyun Seo, Seongnam-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 13/966,401

(22) Filed: Aug. 14, 2013

(65) Prior Publication Data

US 2014/0051140 A1    Feb. 20, 2014

(30) Foreign Application Priority Data

Aug. 14, 2012  (KR) .................. 10-2012-0089156

(51) Int. Cl.
*C12P 7/42* (2006.01)
*C07C 51/16* (2006.01)

(52) U.S. Cl.
CPC . *C12P 7/42* (2013.01); *C07C 51/16* (2013.01); *C12Y 102/01003* (2013.01); *C12Y 401/03038* (2013.01)

(58) Field of Classification Search
CPC ............. C12P 7/42; C12P 7/02; C07C 51/16; C07C 51/235
USPC ................................. 435/136, 475
See application file for complete search history.

(56) References Cited

U.S. PATENT DOCUMENTS

| | | | |
|---|---|---|---|
| 3,985,797 A | 10/1976 | Massie | |
| 4,740,614 A | 4/1988 | Fjare | |
| 5,399,178 A | 3/1995 | Cherpeck | |
| 6,030,819 A | 2/2000 | Amaratunga et al. | |
| 6,555,350 B2 * | 4/2003 | Ahring et al. | 435/162 |
| 6,664,088 B2 * | 12/2003 | Narbad et al. | 435/195 |
| 6,830,899 B1 | 12/2004 | Chen et al. | |
| 7,348,412 B1 | 3/2008 | Parhami-Seren et al. | |
| 2003/0158397 A1 | 8/2003 | Ramos et al. | |
| 2006/0246559 A1 | 11/2006 | Ben-Bassat et al. | |
| 2007/0259409 A1 | 11/2007 | Wery | |

FOREIGN PATENT DOCUMENTS

| | | |
|---|---|---|
| GB | 117498 A | 6/1968 |
| JP | 05-009154 A | 1/1993 |
| JP | 06-078780 A | 3/1994 |
| WO | WO 98/56920 A1 | 12/1998 |
| WO | WO 2005/103273 A1 | 11/2005 |

OTHER PUBLICATIONS

Frost et al., Biocatalytic Syntheses Of Aromatics From D-Glucose: Renewable Microbial Sources of Aromatic Compounds, *Annu. Rev. Microbiol.*, 49: 557-579 (1995).
Narbad et al. Metabolism of ferulic acid via vanillin using a novel CoA-dependent pathway in a newly-isolated strain of *Pseudomonas fluorescens, Micobiology*, 144:1397-1405 (1998).
Siebert et al., Formation of 4-hydroxybenzoate in *Escherichia coli*: characterization of the ubiC gene and its encoded enzyme chorismate pyruvate-lyase, *Microbiology*, 140: 897-904 (1994).
European Patent Office, Extended European Search Report in European Patent Application No. 13180430.4, Dec. 6, 2013, 8 pp.
Barker et al., Microbial Synthesis of p-Hydroxybenzoic Acid from Glucose, *Biotechnology and Bioengineering* 76(4): 376-390 (Dec. 2001).
Ito et al., Expansion of Substrate Specificity and Catalytic Mechanism of Azoreductase by X-ray Crystallography and Site-directed Mutagenesis, *The Journal of Biological Chemistry* 283(20):13889-13896 (May 16, 2008).
Wang et al., Enhancement of the Activity of L-Aspartase from *Escherichia coli* W by Directed Evolution, *Biochemical and Biophysical Research Communications* 276(1): 346-349 (2000).
Whited et al., Toluene-4-Monooxygenase, a Three-Component Enzyme System That Catalyzes the Oxidation of Toluene to p-Cresol in *Pseudomonas mendocina* KR1, *Journal of Bacteriology* 173(9): 3010-3016 (May 1991).
Williams et al., Directed Evolution Of Enzymes For Biocatalysis And The Life Sciences, *Cellular and Molecular Life Sciences* 61: 3034-3046 (2004).
Yuan et al., Laboratory-Directed Protein Evolution, *Microbiology and Molecular Biology Reviews* 69(3): 373-392 (Sep. 2005).

* cited by examiner

*Primary Examiner* — Nashaat Nashed
(74) *Attorney, Agent, or Firm* — Leydig, Voit & Mayer, Ltd.

(57) ABSTRACT

A method of biologically producing p-hydroxybenzoic acid, and a method for producing p-hydroxybenzoic acid from lignin through chemical and biological conversion.

12 Claims, 6 Drawing Sheets

SEQUENCE LISTING

<160> NUMBER OF SEQ ID NOS: 2

<210> SEQ ID NO 1
<211> LENGTH: 29
<212> TYPE: DNA
<213> ORGANISM: Artificial Sequence
<220> FEATURE:
<223> OTHER INFORMATION: Synthetic (Forward primer for ADC lyase)

<400> SEQUENCE: 1
aaacatatgt cactaatgga caattggaa                                29

<210> SEQ ID NO 2
<211> LENGTH: 29
<212> TYPE: DNA
<213> ORGANISM: Artificial Sequence
<220> FEATURE:
<223> OTHER INFORMATION: Synthetic (Reverse primer for ADC lyase)

<400> SEQUENCE: 2
aaactcgaga tattttgtct tcactgttc                                29

PROCESS OF BIOLOGICALLY PRODUCING A P-HYDROXYBENZOIC ACID

CROSS-REFERENCE TO RELATED APPLICATIONS

This application claims the benefit of Korean Patent Application No. 10-2012-0089156, filed on Aug. 14, 2012, in the Korean Intellectual Property Office, the entire disclosure of which is incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 686 Byte ASCII (Text) file named "714070_ST25.txt," created on Aug. 13, 2013.

BACKGROUND OF THE INVENTION

1. Field of the Invention

The present invention relates to a biological process of producing p-hydroxybenzoic acid. Also, the present invention relates to a process of producing p-hydroxybenzoic acid through the chemical and/or biological conversion from lignin as a raw material.

2. Description of the Related Art

Steadily increasing oil prices and an increase in the price of basic fractions, such as naphtha, has given rise to a rapid increase in the price of petrochemical products. As an alternative to the petrochemical industry's dependence on crude oil, industrial biotechnology (also known as white biotechnology) has attracted intensive attention for its use of biomass to produce alternatives to conventional energy and production methods thereof; and additionally for its applications in other fields, including bioenergy, bioplastics, and biocompounds.

The market of bioplastics produced from biomass has rapidly expanded since Cargill-Dow successfully commercialized polylactic acid (PLA) in 2002, which is a substitute for pre-existing plastics, including polyethylene terephthalate (PET) and polystyrene (PS). In addition, polyhydroxyalkanoate (PHA)-based bioplastics, developed and commercialized by Metabolix earlier than PLA, are ready for entry into the market of general-purpose polymers from the market of expensive medical polymers as Metabolix constructed relevant plants. Polybutylene succinate (PBS) products, which involve succinic acid, are also widely commercialized and utilized.

Turning to biochemical products, a successful example of replacing a conventional petrochemical process with an industrial biotechnology process is 1,3-propandiol, commercialized by DuPont in-2006. In the future, industrial biotechnologies for various chemical products are expected to be developed and used in place of conventional petrochemical processes.

Aromatic hydroxycarboxylic acids, particularly p-hydroxybenzoic acid, salicylic acid and 2-hydroxy-3-naphthoic acid, have long been known for utility as raw materials in preservatives, medicines, dyes, pigments, etc. In addition, they have recently drawn extensive attention for utilization as monomers for aromatic polyesters as well as raw materials for agricultural chemicals, and color developing agents of thermal paper. The chemical p-hydroxybenzoic acid is used as a main monomer which accounts for 65% of the liquid crystal polymer Zenite™, manufactured by Ticona. This liquid crystal polymer is widely applied to automotive parts and electronics industries due to its higher than conventional general-purpose resin strength/stiffness, heat stability, organic solvent tolerance, lower melt viscosity, and gas permeability. Moreover, p-hydroxybenzoic acid can be converted via esterification into paraben, which is widely used as a preservative in cosmetics, hygienic goods, daily supplies, and foods.

For chemical synthesis of p-hydroxybenzoic acid, a method based on the Kolbe-Schmitt reaction from phenol and carbon dioxide (JP 05-009154), and modifications thereof (U.S. Pat. Nos. 5,399,178, 4,740,614, 3,985,797) were reported. However, the chemical synthesis methods of p-hydroxybenzoic acid cause various significant problems in production processes, in addition to requiring high production costs. In practice, chemical synthesis methods force workers to face environmental dangers of high temperatures and high pressures, require complex separation and purification procedures for by-products formed after the reaction, and produce environmental pollution due to chemical wastes formed during the separation and purification procedures.

The biological production of p-hydroxybenzoic acid was introduced by the microbial production of p-hydroxybenzoic acid from benzoic acid, p-cresol, toluene, etc. (JP 06-078780, Whited and Gibson, J. Bacteriol. 173:3010-3020 (1991), US20060246559, WO2005/103273). However, the starting materials are toxic to microbes, making the scale-up of the production difficult.

In 1998, DuPont developed a technique for producing p-hydroxybenzoic acid from glucose using *Pseudomonas mendocina* (WO1998/056920). The microbial production of p-hydroxybenzoic acid from glucose was successfully implemented in recombinant *E. coli* by GE in 2000 (U.S. Pat. No. 6,030,819). Ramos et al., of North Carolina State University, succeeded in developing p-hydroxybenzoic acid resistant bacteria containing a *Psudomonas putida*-derived tonB, a p-hydroxybenzoic acid-tolerant gene in 2008 (U.S. Pat. No. 7,348,421). In addition, Frost et al, of Michigan State University, produced p-hydroxybenzoic acid at a concentration of 12 g/L from glucose in *E. coli* in 2001 (Biotechnol Bioeng. (2001) 76(4):376-90).

SUMMARY OF THE INVENTION

The present invention relates to a biological method for the production of p-hydroxybenzoic acid. Specifically, an aspect of the present invention is to provide a method for biologically producing p-hydroxybenzoic acid, comprising: contacting a substrate with a biocatalyst capable of producing p-hydroxybenzoic acid, said substrate including an aromatic carboxylic acid having a) a p-hydroxy group and b) a hydroxy group or C1-C4 alkoxy group attached to at least one other position of the aromatic ring, said biocatalyst having an activity of removing the hydroxy group or C1-C4 alkoxy group of b) to produce the p-hydroxybenzoic acid.

In addition, the present invention relates to a method for producing p-hydroxybenzoic acid from lignin as a raw material through chemical and/or biological conversion. In one embodiment, the present invention provides a method for producing p-hydroxybenzoic acid, comprising degradation of lignin into a breakdown product comprising an aromatic carboxylic acid having a) a p-hydroxy group and b) a hydroxy group or C1-C4 alkoxy group attached to at least one other position of the aromatic ring; and contacting the breakdown product of lignin with a biocatalyst capable of producing p-hydroxybenzoic acid by removing the hydroxy group or C1-C4 alkoxy group of b).

Also contemplated in accordance with the present invention is a method for producing p-hydroxybenzoic acid, comprising degradation of lignin into a breakdown product comprising p-hydroxybenzaldehyde; and oxidizing the breakdown product of lignin to convert p-hydroxybenzaldehyde into p-hydroxybenzoic acid.

In accordance with an aspect thereof, the present invention provides a method for biologically producing p-hydroxybenzoic acid, comprising contacting a substrate with a biocatalyst capable of producing p-hydroxybenzoic acid, said substrate including an aromatic carboxylic acid having a) a p-hydroxy group and b) a hydroxy group or C1-C4 alkoxy group attached to at least one other position of the aromatic ring.

In accordance with another aspect thereof, the present invention provides a method for producing p-hydroxybenzoic acid from a breakdown product of lignin as a raw material through chemical and/or biological conversion.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
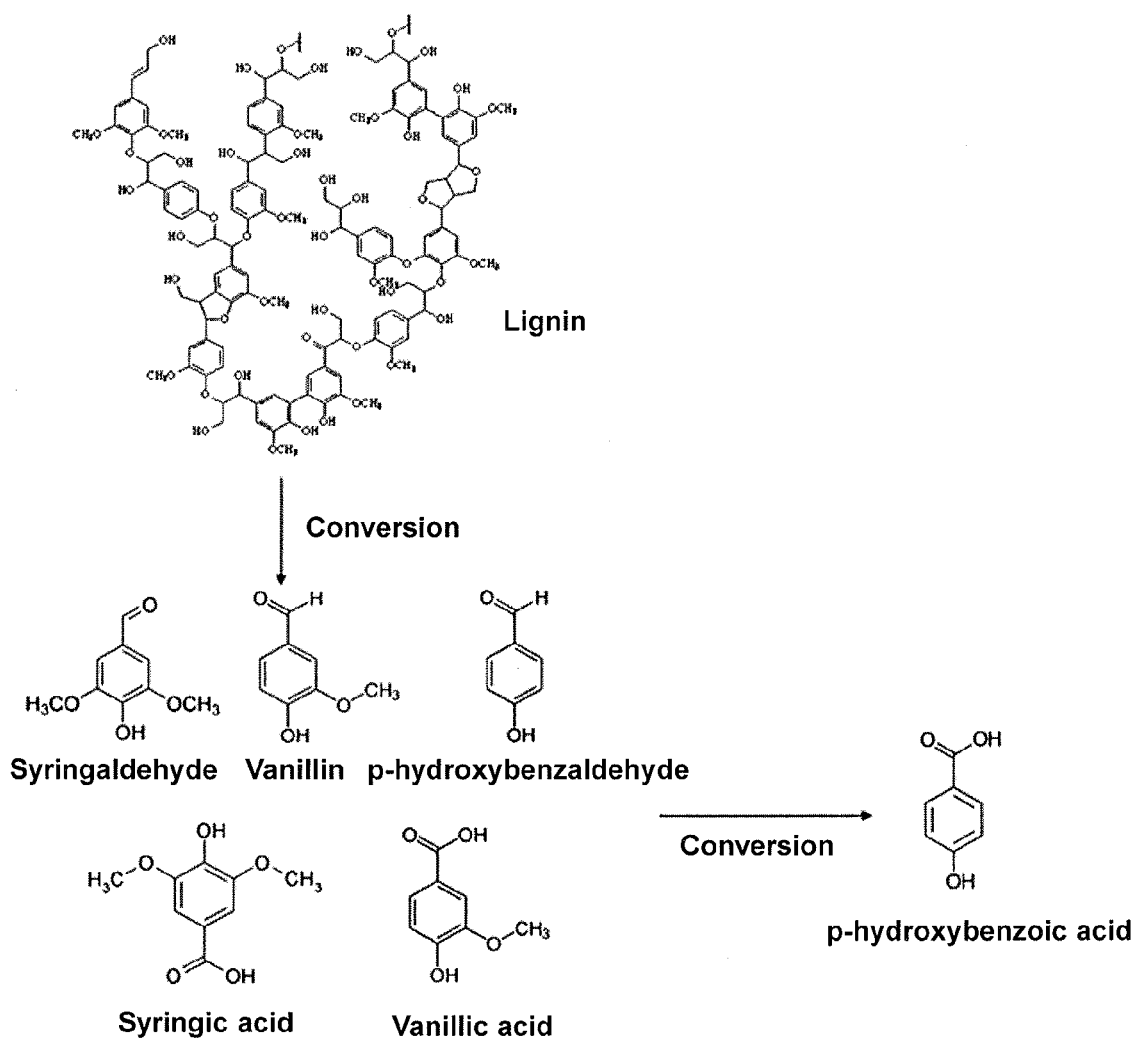
FIG. 1 is a schematic view depicting a production pathway of p-hydroxybenzoic acid from lignin.

As used herein, the term "aromatic carboxylic acid" means an aromatic compound having a carboxylic acid attached to at least one position of the aromatic ring.

In one embodiment of the present disclosure, the aromatic carboxylic acid having a) a p-hydroxy group and b) a hydroxy group or C1-C4 alkoxy group attached to at least one other position of the aromatic ring may be represented by the following Chemical Formula 1, and may be preferably vanillic acid or syringic acid.

[Chemical Formula 1]

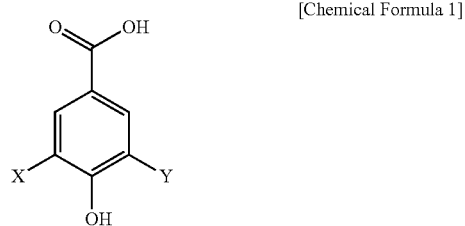

wherein, X and Y, which may be the same or different, are independently hydrogen, hydroxy or C1-C4 alkoxy, with the provision that X and Y are not both hydrogen. The C1-C4 alkoxy is C1-C4 alkyl singular bonded to oxygen wherein the alkyl may be linear or branched. Preferably, the C1-C4 alkoxy is methoxy or ethoxy.

The compound of Chemical Formula 1 is used as a substrate for a biological reaction to produce p-hydroxybenzoic acid. As used herein, the term "biological reaction or conversion" is intended to encompass a biological method using an enzyme, a microorganism containing an enzyme, a lysate of the microorganism, or an extract from the microorganism lysate.

The step of contacting the substrate with the biocatalyst to produce p-hydroxybenzoic acid may be performed by contacting the substrate with an enzyme, a microorganism containing an enzyme, a lysate of the microorganism, or an extract from the microorganism lysate, or culturing the microorganism in a medium containing the substrate.

The biocatalyst has an activity to remove the substituent at position 3' and/or 5' of the benzene ring. So long as it can remove a substituent at position 3' and/or 5' of the benzene ring of the compound represented by Chemical Formula 1 to produce p-hydroxybenzoic acid, any enzyme may be used in the present invention. The enzyme useful in the present invention may be at least one selected from the group consisting of but not limited to, anthranilate synthase (EC 4.1.3.27), 5-O-(1-carboxyvinyl)-3-phosphoshikimate phosphate-lyase (EC 4.2.3.5), chorismate lyase (EC 4.1.3.40), 3-dehydroshikimate hydro-lyase (EC 4.2.1.118), isochorismate lyase (EC 4.2.99.21), aminodeoxychorismate lyase (EC 4.1.3.38), 3-dehydroquinate hydro-lyase (EC 4.2.1.10), prephenate hydro-lyase (EC 4.2.1.51) and hydroxyphenylpyruvate synthase (EC 5.4.99.5).

For example, aminodeoxychorismate lyase (ADC lyase) catalyzes the removal of methoxy at position 3' and/or 5' of a benzene ring from vanillic acid or syringic acid to produce p-hydroxybenzoic acid.

Additional examples of an enzyme useful in the present invention include those enzymes comprising the amino acid sequences encoded by GenBank Nos. AAA35175.1, AA35176.1, AAA23487, CAA47181.1, AAC37159, AAK46749, CAA96313, CAA42091, CAA86380, and AAB59309.

An enzyme may act on various substrates, and even on unknown substrates. In addition, an enzyme's activity may vary from one substrate to another, and an enzyme's activity or specificity may be changed through modifications such as mutation or directed evolution. For instance, Ito et al. reported a change of azoreductase in substrate specificity by mutation at a single amino acid on the basis of structural analysis after they empirically established a three-dimensional structure of *E. coli*-derived azoreductase (Ito et al., Expansion of Substrate Specificity and Catalytic Mechanism of Azoreductase by X-ray Crystallography and Site-directed Mutagenesis, Journal of Biological Chemistry, 283(20), 13889-13896, 2008). In addition, Wang et al., succeeded in developing a mutant aspartase with a 28-fold higher activity than the wild-type by constructing a mutant library of *E. coli*-derived aspartase through error-prone PCR and DNA shuffling (Wang et al., Enhancement of the activity of 1-aspartase from *Escherichia coli* W by directed evolution, Biochemical and Biophysical Research Communications, 276(1), 346-349, 2000). Thus, it is known that enzymes can be changed in substrate specificity or enhanced in activity using protein evolution technology. There are reports of practical applications of modified enzymes to reaction engineering (Williams et al., Directed evolution of enzymes for biocatalysis and the life sciences, Cellular and Molecular Life Sciences, 61, 3034-3046, 2004), and various experiments for protein evolution are also known (Yuan et al., Laboratory-Directed Protein Evolution, Microbiology and Molecular Biology Review, 69(3), 373-392, 2005).

In one embodiment of the present invention, the enzyme may be modified or evolved to have an increased substrate specificity or enzymatic activity to vanillic acid or syringic acid, thereby enhancing the production of p-hydroxybenzoic acid.

In another embodiment of the present invention, the enzyme may be derived from an eukaryote selected from the group consisting of, but not limited to, *Saccharomyces, Zygosaccharomyces, Schizosaccharomyces, Kluyveromyces, Candida, Hansenula, Debaryomyces, Nadsonia, Lipomyces, Torulopsis, Kloekera, Pichia, Trigonopsis, Brettianomyces, Aspergillus, Yarrowia, Cryptococcus, Aureobasidium, Rhizopus, Monascus, Leucosporidium*, and *Issatchenkia*, or a prokaryote selected from the group consisting of, but not limited to, *Streptococcus, Escherichia, Bacillus, Brucella, Mycobacterium, Salmonella, Shigella, Yersinia, Aquifex, Helicobacter, Staphylococcus, Thermotoga, Pseudomonas, Sinorhizobium, Vibrio, Schizosaccharomyces, Clostridium, Lactobacillus, Klebsiella, Citrobacter*, and *Streptomyces*. In detail, the enzyme may be derived from *Escherichia coli, Streptococcus pneumonia, Bacillus subtilis, Brucella suis, Mycobacterium tuberculosis, Salmonella enteric, Yersinia enterocolitica, Helicobacter pylori, Staphylococcus aureus, Pseudomonas putida, Vibrio harveyi, Clostridium beijerinckii, Lactobacillus rhamnosus, Saccharomyces cerevisiae*, or *Klebsiella pneumonia*.

In a further embodiment of the present invention, the microorganism involved in the conversion of the compound of Chemical Formula 1 into p-hydroxybenzoic acid may be recombinant or wild-type. A recombinant microorganism might be prepared by introducing a gene encoding an enzyme into a host cell using a recombinant technique.

When a recombinant microorganism is used according to one embodiment of the present invention, the method comprises 1) constructing an expressing vector carrying a gene coding for an enzyme; 2) transforming the expression vector into a host cell, followed by culturing the host cell; 3) producing the enzyme from the host cell; and 4) reacting the enzyme with the substrate.

Any expression vector that is employed in genetic manipulation could be applied to the construction of the recombinant expression vector for use in producing p-hydroxybenzoic acid. So long as it can be transformed with the recombinant expression vector to expresses the gene of interest to produce an active enzyme protein, any strain, whether bacterial, fungal, or yeast, can be used as a host cell in the present invention. A preferred host cell is *E. coli*.

When the biocatalyst capable of producing p-hydroxybenzoic acid is an enzyme, the enzymatic reaction may be done at a pH of from 5.5 to 9.5, with an optimal pH dependent on the enzyme used. In one embodiment of the present invention, the conversion may be conducted at a pH of 7.0 to 7.6. In addition, the enzymatic reaction may be done at a temperature of from 25° C. to 50° C., with the optimal temperature depending on the enzyme employed. In a preferred embodiment of the present invention, conversion from the aromatic carboxylic acid to p-hydroxybenzoic acid is executed at 30° C.-37° C. As for the reaction time, its control can be achieved in a typical manner known in the art.

In accordance with another embodiment of the present invention, the method may further comprise oxidizing an aromatic aldehyde represented by Chemical Formula 2 into an aromatic carboxylic acid of Chemical Formula 1 prior to contact between the substrate and the biocatalyst. Preferably, the aromatic aldehyde of Chemical Formula 2 may be vanillin or syringaldehyde:

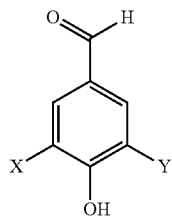

[Chemical Formula 2]

wherein X and Y, which may be the same or different, are independently hydrogen, hydroxy or C1-C4 alkoxy, with the provision that X and Y are not both hydrogen. The C1-C4 alkoxy is C1-C4 alkyl singular bonded to oxygen wherein the alkyl may be linear or branched. Preferably, the C1-C4 alkoxy is methoxy or ethoxy.

In accordance with another aspect thereof, the present invention addresses a method for producing p-hydroxybenzoic acid from a lignin breakdown product as a raw material through chemical and/or biological conversion.

The substrate including an aromatic carboxylic acid having a) a p-hydroxy group and b) a hydroxy group or C1-C4 alkoxy group attached to at least one other position of the aromatic ring, or a compound of Chemical Formula 1 or 2 can be obtained by degrading lignin.

If the breakdown product obtained by degrading lignin contains the aromatic aldehyde compound of Chemical Formula 2, the lignin breakdown product may be oxidized into the aromatic carboxylic acid of Chemical Formula 1 before it is brought into contact with the biocatalyst.

In accordance with a further aspect thereof, the present invention addresses a method for producing p-hydroxybenzoic acid, comprising: degrading lignin to provide a lignin breakdown product containing p-hydroxybenzaldehyde; and oxidizing the lignin breakdown product into p-hydroxybenzoic acid.

Focusing on the synthesis of p-hydroxybenzoic acid from biomass, the present invention is configured to chemically or biologically degrade lignin, an inexpensive raw material, into aromatic monomers and to chemically or biologically convert the aromatic monomers into p-hydroxybenzoic acid, thus eliminating dependence on petrochemical materials.

Within the scope of the lignin of the present invention, are lignin, lignin derivatives, lignin fragments, and lignin-containing material. The term "lignin derivatives," as used herein, is intended to encompass lignin compounds modified by a chemical reaction, such as phenolation, acetylation, etc. The term "lignin fragments" means breakdown products obtained as a result of the chemical or biological degradation of lignin.

Typically, lignin is obtained by separating cellulose and hemicelluloses in a biorefinery or pulping process. There are various types of lignin including Kraft lignin (alkaline lignin), dealkaline lignin, hydrolytic lignin, organosolv lignin, and sodium lignin sulfonate, according to the production process. As a by-product from the lignocelluloses bioethanol process, lignin can be also used Lignin is an aromatic polymer surrounding microfibers, forming a resinous structure in which phenylpropanoids, such as coumaryl alcohol, coniferyl alcohol, sinapyl alcohol, etc. serve as structural units, being polymerized via carbon-carbon bonds or carbon-oxygen bonds in a haphazard manner The degradation of lignin may be biodegradation or physicochemical degradation, the latter being preferred because of higher degradation rate.

Biodegradation of lignin may be carried out with enzymes such as peroxidase and laccase.

Among the types physicochemical degradation available for lignin in the present invention are pyrolysis, gasification, hydrogenolysis, acidolysis, alkaline lysis, chemical oxidation, and hydrolysis under supercritical condition.

In one embodiment, the acidolysis or alkaline lysis of lignin is preferably accomplished by treatment with a high concentration (0.5 to 2.0 M) solution of NaOH or KOH or with $H_2SO_4$, HCl, or $HNO_3$ at a concentration of 0.1 to 5% (w/v). Preferably, the acidic or alkaline treatment is carried out at about 80~350° C. for 5~120 min.

Turning to pyrolysis, lignin can be degraded at as high as 350~650° C. using a high pressure reactor. The efficiency of pyrolysis can be increased in the presence of a catalyst such as nitrobenzene, $KMnO_4$, $H_2O_2$, zeolite, etc. In addition, the degradation of lignin can be accomplished using other physicochemical such as hydrogenolysis and hydrolysis under supercritical condition.

For optimization, the degradation of lignin is preferably carried out at an oxygen pressure of 2-20 bar. In addition, the degradation processes are preferably completed within 200 min, but the duration may be adjusted appropriately.

The lignin breakdown products include a mixture of aromatic monomers, such as vanillin, syringaldehyde, p-hydroxybenzaldehyde, vanillic acid, syringic acid, etc., and contain compounds of Chemical Formula 1 and/or 2.

For example, conversion from the aromatic aldehyde of Chemical Formula 2 to the aromatic carboxylic acid of Chemical Formula 1 may be of chemical or biological reaction.

For chemical conversion, a silver oxide method or a caustic fusion method may be utilized. First, aromatic monomers with an aldehyde functional group are reacted with 1 M NaOH at 55~60° C. for about 10 min in the presence of 1 M $Ag_2O$, followed by neutralization with the equal amount of 1 M HCl with agitation to afford the aromatic carboxylic acid as a precipitate.

The biological conversion is characterized by the use of a biocatalyst such as an enzyme, a whole microbial cell, a microbial cell lysate, or a cell extract. The enzyme useful in the present invention may be exemplified by aldehyde dehydrogenase (EC 1.2.1.3, EC 1.2.1.4, EC 1.2.1.5), vanillin dehydrogenase (EC 1.2.1.67) and other enzymes functionally corresponding thereto. Non-limiting examples of these enzymes include GenBank ID CAD60262.1, ABK09332.1, Uniprot ID P47771, and P54114. Reactions in the presence of a pure enzyme as well as a microbial whole cell expressing the enzyme or functionally identical enzymes, such as *Saccharomyces cerevisiae*, *Bacillus subtilis*, *Escherichia coli*, *Pseudomonas fluorescens*, *Pseudomonas putida*, *Serratia marcescens*, *Sphingomonas paucimobilis*, *Streptomyces viridosporus*, *Desulfovibrio vulgaris*, or *Burkholderia cepacia*, or a lysate or extract thereof are considered as the enzymatic reaction.

The biological conversion may be a reaction in which the aromatic aldehyde of Chemical Formula 2 is brought into contact with a suitable enzyme or a microorganism containing the enzyme or in which the microorganism is cultured in a medium containing the aromatic aldehyde. This enzymatic reaction may be conducted at a pH range of from 5.5 to 9.5, with an optimal pH dependent on the enzyme used. Further, in one embodiment of the present invention, the enzymatic reaction may be done at a temperature of from 25° C. to 50° C., with the optimal temperature depending on the enzyme employed. In a preferred embodiment of the present invention, the conversion is executed at 30° C.~37° C.

Characterized by a biological process in which a substrate is contacted with a biocatalyst, the present invention allows p-hydroxybenzoic acid to be produced in an environment-friendly manner and at higher specificity, compared to a chemical process.

In addition, the present invention provides the production of p-hydroxybenzoic acid from lignin, a renewable biomass. In this regard, lignin may be chemically degraded to give lignin breakdown products including aromatic monomers, followed by biological conversion of the breakdown products into p-hydroxybenzoic acid.

EXAMPLES

A better understanding of the present invention may be obtained through the following examples which are set forth to illustrate, but are not to be construed as limiting the present invention.

<Analysis of Aromatic Monomers Derived from Lignin>

Figure 2:
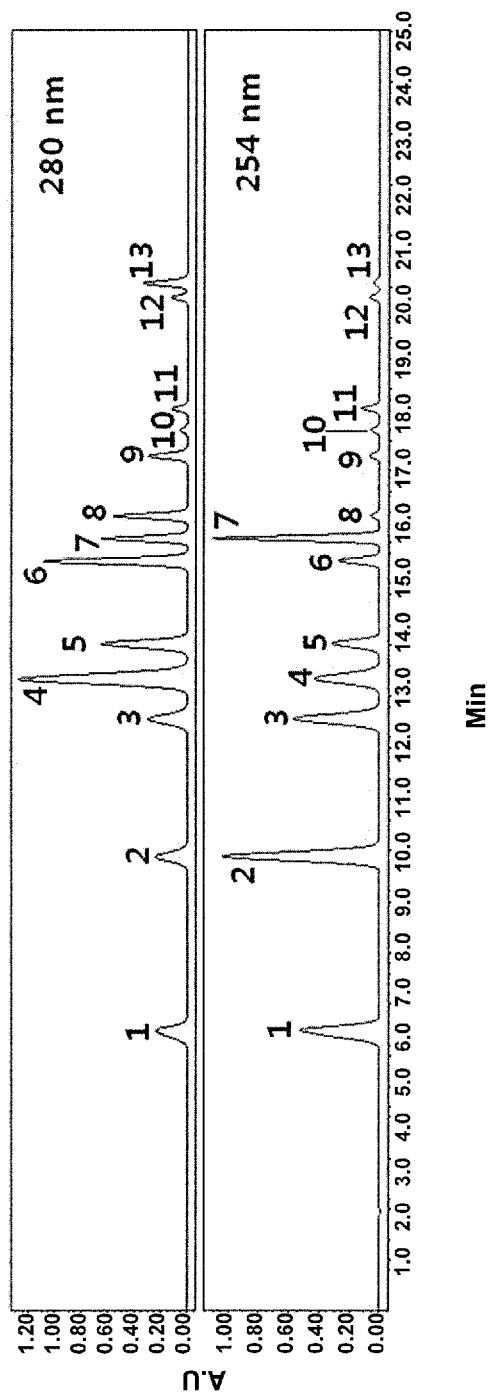
FIG. 2 is a set of HPLC chromatograms of lignin-derived aromatic monomers and standard materials.

For use in the quantitative analysis of lignin-derived aromatic monomers, standard solutions of 13 materials including vanillin and p-hydroxybenzoic acid were prepared, and analyzed using Waters e2695 HPLC equipped with a Waters 2489 UV/VIS (254 nm, 280 nm) detector (FIG. 2). For analysis, an XBridge C18 column (4.6×150 mm, 5 μm) was employed, and maintained at 35° C., with a mobile phase moved at 1 mL/min The mobile phase was a mixture of A) a 5% acetonitrile solution containing 0.1% formic acid, and B) and a 50% acetonitrile solution containing 0.1% formic acid, and was applied in the following gradient elution manner 1.5 min (0% B), 9.5 min (90% B), 16.5 min (40% B), 21.5 min (24% B), and 24.5 min (0% B). Prior to subsequent analysis, the column was pre-equilibrated for 6 min.

In the chromatograms of FIG. 2, the compound corresponding to each peak is as follows:
1. 3,4-dihydroxybenzoic acid
2. p-hydroxybenzoic acid
3. vanillic acid
4. p-hydroxybenzaldehyde
5. syringic acid
6. vanillin
7. coniferyl alcohol
8. syringaldehyde
9. guaiacol
10. 2,6-dimethoxy phenol
11. benzoic acid
12. 2,6-dimethoxy-4-methylphenol
13. 2-methoxy-4-methylphenol The generation of p-hydroxybenzoic acid was monitored using HPLC and ESI-MS/MS (Waters TQD). This HPLC was conducted in the same condition as in the above HPLC. The condition for mass spectrometry was optimized with a p-hydroxybenzoic acid standard solution. Mass spectra were obtained in the positive mode and the optimal condition for the spectrometry was set forth as follows: Capillary voltage: 3 kV, Cone voltage: 25 V, Source temperature: 120° C., Desolvation temperature: 300° C., Desolvation gas flow: 600 L/hr (N2), and Cone gas flow: 60 L/hr (N2). On the HPLC-ESI-MS/MS spectra, a peak for p-hydroxybenzoic acid was detected, in comparison with the standard solution, in the scan mode (50~200, m/z) as molecular ions and specific fragment ions were generated at a given collision energy.

Example 1

Degradation of Lignin by Alkaline Oxidation

Figure 3:
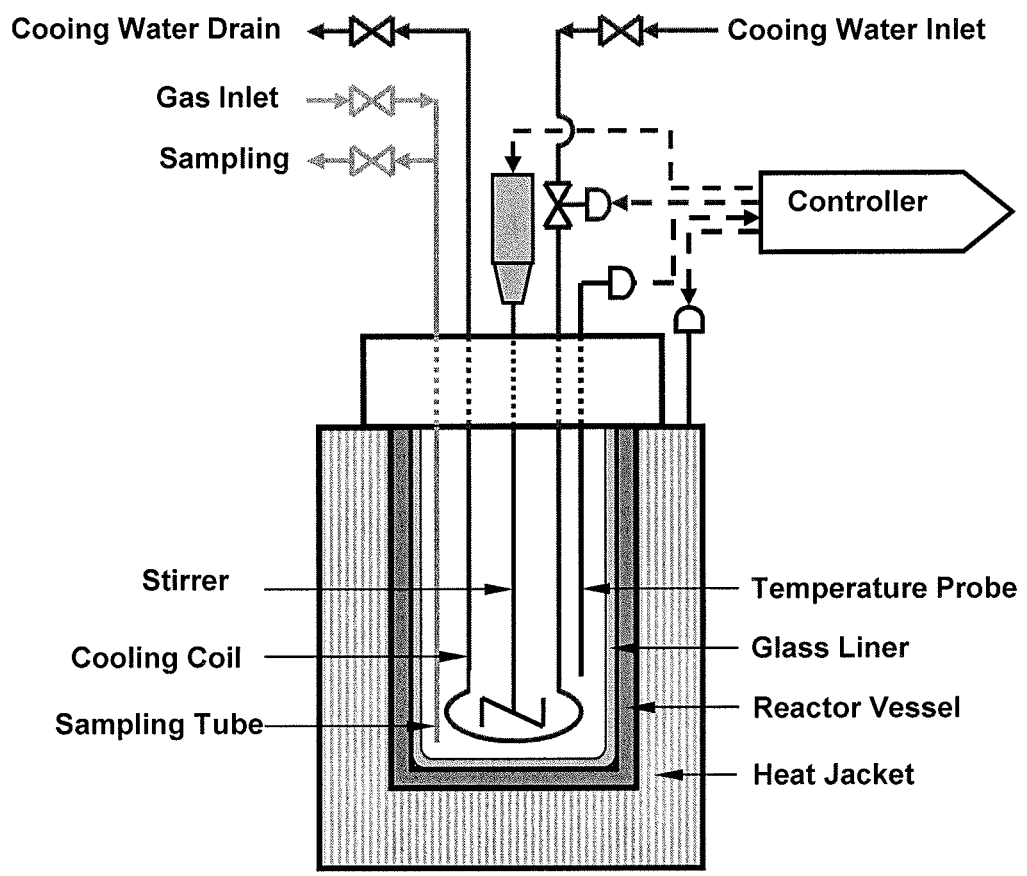
FIG. 3 is a schematic view of a high-pressure reactor (450 mL, Parr 4562) available for pyrolysis in accordance with an embodiment of the present invention.

Lignin was degraded using a laboratory high-pressure reactor (450 mL, Parr 4562) shown in FIG. 3. A reactant with a lignin content of 5.0% (w/v) was prepared by adding 10.0 g of Kraft lignin to 200 mL of 1 M NaOH. The reactant was further mixed with 10 g of the catalyst $KMnO_4$, loaded to a stainless steel high-pressure reactor with an internal volume of 450 mL, sealed, and stirred at a speed of 500 rpm. After the reactor was filled with oxygen gas at a pressure of about 5 bar for 2 min via a sampling line communicating with the interior thereof; it started to be heated. When the internal temperature of the reactor reached 140° C., the reaction was continued for 60 min. The reaction temperature was adjusted by a PID controller through a cooling water tube. At 60 min of the reaction, a sample was withdrawn via a sampling line, and then, the reaction was terminated.

Two mL of the sample containing alkaline breakdown products of lignin was 3-fold diluted with 4 mL of distilled water, followed by removal of lignin by filtration (10 kDa MWCO). To 1 mL of the lignin-free sample were added 9 volumes of methanol, and lignin breakdown products were purified by filtration through a syringe filter (0.22 μm). The filtrate was analyzed by HPLC, and the composition thus obtained is summarized in Table 1, below.

TABLE 1

| Composition | Concentration (mM) |
| --- | --- |
| p-hydroxybenzoic acid | 0.00 |
| p-hydroxybenzaldehyde | 0.66 |
| vanillic acid | 1.90 |
| Vanillin | 5.32 |
| syringic acid | 0.20 |
| Syringaldehyde | 0.11 |

Example 2

Production of p-Hydroxybenzoic Acid by Enzymatic Reaction

<Step 1> Construction of Recombinant Expression Vector Carrying Aminodeoxychorismate Lyase Gene and Preparation of Transformed Microorganism To produce aminodeoxychorismate lyase (ADC lyase), an ADC lyase gene from *S. cerevisiae* was cloned. First, genomic DNA was isolated from *S. cerevisiae* KCCM 50712. On the basis of a nucleotide sequence (GenBank Accession Number; DAA10190.1) coding for the ADC lyase of *S. cerevisiae* KCCM 50712, the following primers were designed:

```
(Forward primer):
5'-AAACATATGTCACTAATGGACAATTGGAA-3' (SEQ ID NO: 1)

(Reverse primer):
5'-AAACTCGAGATATTTTGTCTTCACTGTTC-3' (SEQ ID NO: 2)
```

The nucleotide sequence of ADC lyase gene was amplified by PCR using the primers, with the genomic DNA of *S. cerevisiae* KCCM 50712 serving as a template.

A total volume of 50 μl of a PCR composition contained 100 ng of the template, 10 pmol of each primer, 2.5 mM dNTPs, a 1× PCR buffer, and a 2.5 U Taq polymerase. PCR started with pre-denaturation at 94° C. for 5 min, and was performed with 30 cycles of denaturation at 94° C. for 1 min; annealing at 55° C. for 30 sec; and elongation at 72° C. for 3 min, followed by post-polymerization at 72° C. for 5 min for final elongation.

The PCR product thus obtained was digested with NdeI/XhoI restriction enzymes, and inserted in the presence of T4 DNA ligase into the plasmid vector pET28a (Novagen) which was previously cut with the same enzymes, to construct a recombinant pET28a/ADCL vector. PCR and cloning results were monitored by 1.2% agarose electrophoresis.

The recombinant expression vector was typically transformed into *E. coli* BL21 (DE3), and the transformant was cryo-preserved in 15% glycerol until use for enzyme expression.

<Step 2> Production of ADC Lyase

To produce ADC lyase in a large amount, the cryo-preserved recombinant *E. coli* was inoculated into 5 mL of LB broth in a test tube, and seed cultured at 37° C. with agitation to an absorbance of 2.5 at 600 nm. Then, the seed culture was added to 100 mL of LB broth in a 300 mL flask and incubated. When absorbance at 600 nm reached 0.6, 0.5 mM IPTG was added to induce the expression of the enzyme. In this regard, the cells were cultured at 33° C. with agitation at 250 rpm, and further incubated for 6 hrs after IPTG addition.

Then, the transformed cell culture was centrifuged at 4,000 g and 4° C. for 20 min, washed twice with a PBS buffer, mixed with a 50 mM Tris-HCl buffer (pH 7.5) before ultrasonication disruption. The cell lysate was again centrifuged at 13,000 g and 4° C. for 20 min, and the supernatant was withdrawn and subjected to Ni-NTA His-Tag chromatography to purify the enzyme. The bound enzyme was eluted with a 50 mM Tris-HCl buffer (pH 7.5) using a centrifugal separation filter (10 kDa). After concentration, the eluate was quantitatively analyzed using a protein assay (Bradford). Finally, the enzyme was obtained at a concentration of 5 mg/mL, and used to produce p-hydroxybenzoic acid.

<Step 3> Production of p-Hydroxybenzoic Acid

The 5 mg/L ADC lyase was mixed at a volume ratio of 4:1 with 500 mg/L vanillic acid (Sigma) and reacted with each other for 3 hrs in a 37° C. incubator. After completion of the reaction, nine volumes of methanol were added to the reaction mixture which was then filtered through a syringe filter (0.22 μm) to remove impurities. An examination was made of the concentration of p-hydroxybenzoic acid in the resulting sample using HPLC, and the results are given in Table 2.

In addition, syringic acid (Sigma) was also subjected to the same enzymatic reaction, and the results are given in Table 3.

TABLE 2

| Material | Concentration before enzyme reaction (mM) | Concentration after enzyme reaction (mM) |
| --- | --- | --- |
| Vanillic acid | 0.583 | 0.460 |
| p-hydroxybenzoic acid | 0.000 | 0.112 |

TABLE 3

| Material | Concentration before enzyme reaction (mM) | Concentration after enzyme reaction (mM) |
| --- | --- | --- |
| Syringic acid | 0.595 | 0.490 |
| p-hydroxybenzoic acid | 0.000 | 0.068 |

As is understood from the data of Tables 2 and 3, vanillic acid or syringic acid is converted into p-hydroxybenzoic acid by ADC lyase.

Example 3

Production of p-Hydroxybenzoic Acid Using Whole Cell

In place of purified enzyme, whole cells were used to produce p-hydroxybenzoic acid from vanillin.

For this, *S. cerevisiae* KCCM 50712 was incubated at 37° C. and 250 rpm for 24 hrs in a YPD medium containing glucose, and the cell culture was centrifuged at 4,000 g and 4° C. for 20 min. After the cell pellet thus formed was washed twice with a Tris-HCl buffer, the cells were incubated at 37° C. for 24 hrs in a Tris-HCl buffer containing 500 mg/L vanillin as substrate. After completion of the incubation, the culture was extracted with nine volumes of methanol, and the extract was filtered through a syringe filter (0.22 μm). Concentrations of p-hydroxybenzoic acid in the filtrate were examined by HPLC (Table 4).

TABLE 4

|  | Concentration before enzyme reaction (mM) | Concentration after enzyme reaction (mM) |
| --- | --- | --- |
| p-hydroxybenzoic acid | 0.000 | 0.018 |
| Vanillic acid | 0.000 | 0.257 |
| Vanillin | 0.650 | 0.133 |

As is apparent from the data of Table 4, vanillin is converted into vanillic acid and further into p-hydroxybenzoic acid by aldehyde dehydrogenase and ADC lyase present in the whole cell.

Example 4

Production of p-Hydroxybenzoic Acid from Lignin

The lignin breakdown products obtained in Example 1 were enzymatically converted into p-hydroxybenzoic acid. In this regard, a solution of the lignin breakdown products was adjusted to pH 7.5 using a small amount of 10 M HCl, and filtered through a 10 kDa MWCO filter. Separately, a whole cell solution of wild-type *S. cerevisiae* KCCM 50712 of Example 3 containing ADC lyase and aldehyde dehydrogenase was mixed at a volume ratio of 1:1 with the enzyme solution of Example 2. This mixture was mixed at a volume ratio of 4:1 with the filtrate of lignin breakdown products, and reacted for 3 hrs in a 37° C. incubator. After completion of the reaction, the reaction mixture was centrifuged at 13,000 g and 4° C. for 20 min, and the supernatant was extracted with nine volumes of methanol. The extract was filtered through a syringe filter (0.22 μm). Concentrations of p-hydroxybenzoic acid in the filtrate were examined by HPLC (FIG. 4). Analysis results of samples before and after the reaction are summarized in Table 5, below.

Figure 4A:
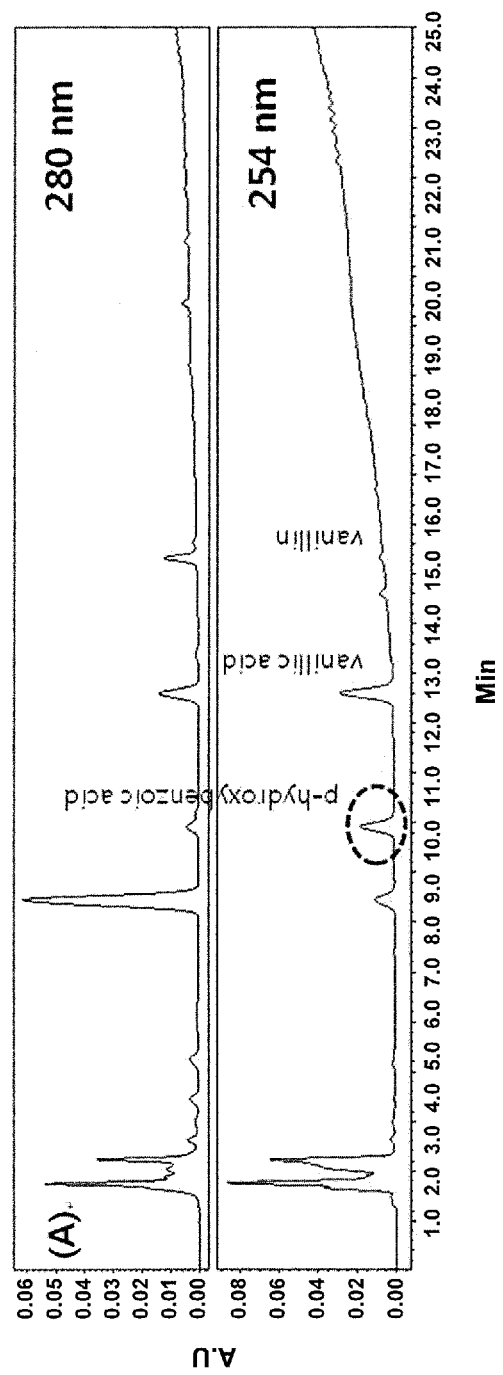
FIG. 4. are (a) HPLC, (b) LC/ESI-MS, and (c) LC/ESI-MS/MS spectra of the products obtained using the method of the present invention.
Figure 4B:
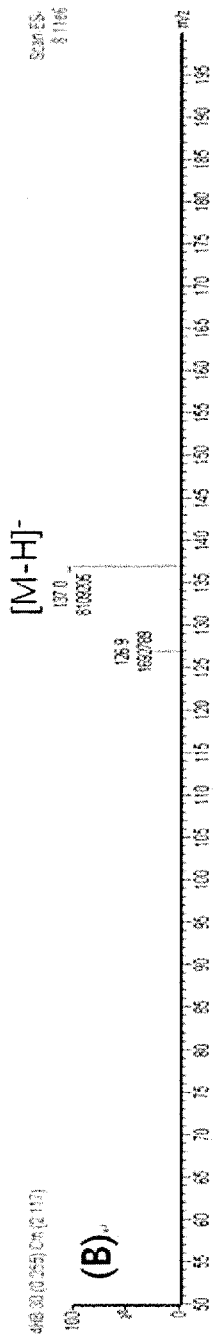
Figure 4C:
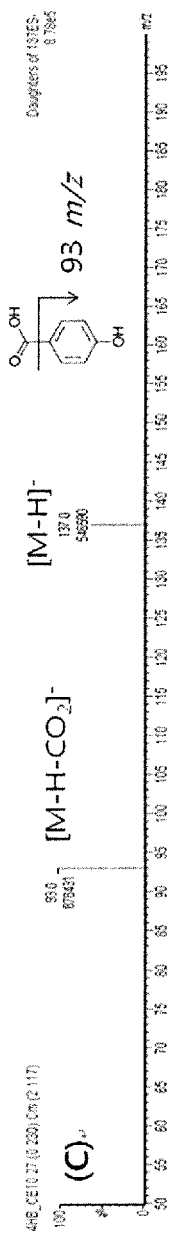

FIG. 4a provides chromatograms showing results of the enzymatic reaction, FIG. 4b is a mass spectrum in the scan mode of a p-hydroxybenzoic acid peak after the enzymatic reaction (M: molecular weight), and FIG. 4c is an MS/MS spectrum of molecular ions of p-hydroxybenzoic acid after the enzymatic reaction.

TABLE 5

| Material | Concentration before enzyme reaction (mM) | Concentration after enzyme reaction (mM) |
| --- | --- | --- |
| p-hydroxybenzoic acid | 0.00 | 1.16 |
| p-hydroxybenzaldehyde | 0.66 | 0.00 |
| Vanillic acid | 1.90 | 4.28 |
| Vanillin | 5.32 | 1.58 |
| syringic acid | 0.20 | 0.00 |
| Syringaldehyde | 0.11 | 0.00 |

As can be seen in the Table 5, lignin breakdown products contain p-hydroxybenzaldehyde, vanillic acid, vanillin, syringic acid and syringaldehyde. Vanillic acid and syringic acid were converted to p-hydroxybenzoic acid by ADC lyase. Vanillin, p-hydroxybenzaldehyde and syringaldehyde were first oxidized by aldehyde dehydrogenase to vanillic acid, p-hydroxybenzoic acid and syringic acid, respectively. The resulting vanillic acid and syringic acid were further converted to p-hydroxybenzoic acid by ADC lyase.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for biologically producing p-hydroxybenzoic acid, comprising:

contacting a substrate with a biocatalyst, wherein the substrate is a lignin-degradation product that comprises an aromatic carboxylic acid having (a) a p-hydroxy group and (b) a hydroxyl group or C1-C4 alkoxy group attached to at least one other position of the aromatic ring, and the biocatalyst comprises a purified enzyme that removes the hydroxyl group or C1-C4 alkoxy group of (b) to produce p-hydroxybenzoic acid; a recombinant microorganism transformed with an expression vector encoding the enzyme; or a lysate of the recombinant microorganism, or an extract of the recombinant microorganism lysate, comprising the enzyme wherein the enzyme is anthranilate synthase (EC 4.1.3.27), 5-O-(1-carboxyvinyl)-3-phosphoshikimate phosphate-lyase (EC 4.2.3.5), chorismate lyase (EC 4.1.3.40), 3-dehydroshikimate hydrolyase (EC 4.2.1.118), isochorismate lyase (EC 4.2.99.21), aminodeoxychorismate lyase (EC 4.1.3.38), 3-dehydroquinate hydro-lyase (EC 4.2.1.10), prephenate hydro-lyase (EC 4.2.1.51), or hydroxyphenylpyruyate synthase (EC 5.4.99.5).

2. The method of claim 1, wherein the aromatic carboxylic acid is represented by Chemical Formula 1:

[Chemical Formula 1]

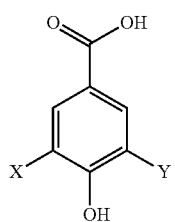

wherein X and Y may be the same or different and are independently hydrogen, hydroxy, or C1-C4 alkoxy, with the provision that X and Y are not both hydrogen.

3. The method of claim 1, wherein the aromatic carboxylic acid is vanillic acid or syringic acid.

4. The method of claim 1, wherein the recombinant microorganism is from *Saccharomyces, Zygosaccharomyces, Schizosaccharomyces, Kluyveromyces, Candida, Hansenula, Debaryomyces, Nadsonia, Lipomyces, Torulopsis, Kloekera, Pichia, Trigonopsis, Brettianomyces, Aspergillus, Yarrowia, Cryptococcus, Aureobasidium, Rhizopus, Monascus, Leucosporidium, Issatchenkia, Streptococcus, Escherichia, Bacillus, Brucella suis, Mycobacterium, Salmonella, Shigella, Yersinia, Aquifex, Helicobacter, Staphylococcus, Thermotoga, Pseudomonas, Sinorhizobium, Vibrio, Schizosaccharomyces, Clostridium, Lactobacillus, Klebsiella, Citrobacter,* or *Streptomyces*.

5. The method of claim 1, wherein the biocatalyst is a recombinant microorganism, and the degradation product is contacted with the biocatalyst by culturing the recombinant microorganism in a medium containing the degradation product.

6. The method of claim 2, wherein the degradation product comprises an aromatic aldehyde represented by Chemical Formula 2, and the method further comprises oxidizing the aromatic aldehyde represented by Chemical Formula 2 to provide the aromatic carboxylic acid of Chemical Formula 1 prior to contacting the degradation product with the biocatalyst:

[Chemical Formula 2]

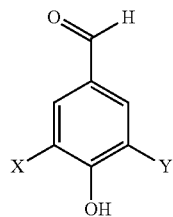

wherein, X and Y may be the same or different and are independently hydrogen, hydroxy or C1-C4 alkoxy, with the provision that X and Y are not both hydrogen.

7. The method of claim 6, wherein the aromatic aldehyde is vanillin or syringaldehyde.

8. The method of claim 6, wherein the aromatic aldehyde is oxidized to provide the aromatic carboxylic acid of Chemical Formula 1 using a chemical catalyst or a biocatalyst.

9. A method for biologically producing p-hydroxybenzoic acid, the method comprising:

degrading lignin into a degraded product comprising an aromatic carboxylic acid having (a) a p-hydroxy group and (b) a hydroxy group or C1-C4 alkoxy group attached to at least one other position of the aromatic ring; and contacting the degraded product with a biocatalyst; wherein the biocatalyst comprises a purified~enzyme that removes the hydroxyl group or C1-C4 alkoxy group of (b) to produce p-hydroxybenzoic acid; a recombinant microorganism transformed with an expression vector encoding the enzyme; or a lysate of the recombinant a microorganism, or an extract of the recombinant microorganism lysate, comprising the enzyme;

wherein the enzyme is anthranilate synthase (EC 4.1.3.27), 5-O-(1-carboxvvinyl)-3-phosphoshikimate phosphate-lyase (EC 4.2.3.5), chorismate lyase (EC 4.1.3.40), 3-dehydroshikimate hydrolyase (EC 4.2.1.118), isochorismate lyase (EC 4.2.99.21), aminodeoxychorismate lyase (EC 4.1.3.38), 3-dehydrominate hydro-lyase (EC 4.2.1.10), prephenate hydro-lyase (EC 4.2.1.51), or hydroxyphenylpyruvate synthase (EC 5.4.99.5).

10. The method of claim 9, wherein the aromatic carboxylic acid is represented by Chemical Formula 1:

[Chemical Formula 1]

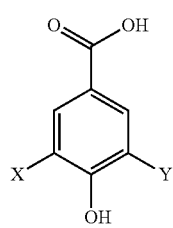

wherein, X and Y may be the same or different and are independently hydrogen, hydroxy or C1-C4 alkoxy, with the provision that X and Y are not both hydrogen.

11. The method of claim 9, wherein degrading lignin into a degraded product comprising an aromatic carboxylic acid comprises degrading lignin into a degraded product comprising an aromatic aldehyde represented by Chemical Formula 2, and oxidizing the aromatic aldehyde represented by Chemical Formula 2 to provide the degraded product comprising the aromatic carboxylic acid of Chemical Formula 1, prior to contacting the degraded product comprising the aromatic carboxylic acid with the biocatalyst:

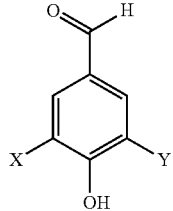
[Chemical Formula 2]

wherein, X and Y may be the same or different and are independently hydrogen, hydroxy or C1-C4 alkoxy, with the provision that X and Y are not both hydrogen.

12. The method of claim 9, wherein the lignin is degraded using pyrolysis, gasification, hydrogenolysis, acidolysis, alkaline lysis, chemical oxidation, hydrolysis, or combination thereof, under supercritical conditions.

* * * * *